(12) United States Patent
Gibbs

(10) Patent No.: US 7,235,390 B2
(45) Date of Patent: Jun. 26, 2007

(54) NUTRIENT ABSORPTION ENHANCING COMPOSITIONS AND METHODS

(75) Inventor: Tracy Gibbs, Draper, UT (US)

(73) Assignee: Health Education Corporation, Draper, UT (US)

( * ) Notice: Subject to any disclaimer, the term of this patent is extended or adjusted under 35 U.S.C. 154(b) by 0 days.

(21) Appl. No.: 10/806,669

(22) Filed: Mar. 22, 2004

(65) Prior Publication Data

US 2004/0247618 A1    Dec. 9, 2004

Related U.S. Application Data

(63) Continuation of application No. 09/989,980, filed on Nov. 20, 2001, now abandoned.

(51) Int. Cl.
*C12N 9/00* (2006.01)

(52) U.S. Cl. .................................... 435/183

(58) Field of Classification Search ................ 435/183
See application file for complete search history.

(56) References Cited

U.S. PATENT DOCUMENTS

| | | | |
|---|---|---|---|
| 3,615,687 A * | 10/1971 | Mochizuki et al. | |
| 4,378,434 A * | 3/1983 | Prentice et al. | |
| 5,447,732 A | 9/1995 | Tanimoto et al. | |
| 5,501,857 A | 3/1996 | Zimmer | |
| 5,597,585 A * | 1/1997 | Williams et al. | |
| 5,759,520 A * | 6/1998 | Sachetto | |
| 5,785,977 A * | 7/1998 | Breithbarth | |
| 5,817,350 A | 10/1998 | Rhode, Jr. et al. | |
| 5,902,617 A * | 5/1999 | Pabst | |
| 5,972,382 A | 10/1999 | Majeed et al. | |
| 5,977,175 A | 11/1999 | Lin | |
| 5,989,600 A | 11/1999 | Nielsen et al. | |
| 5,993,806 A | 11/1999 | Galle | |
| 6,020,351 A * | 2/2000 | Pero | |
| 6,042,823 A * | 3/2000 | Kimura et al. | |
| 6,103,756 A * | 8/2000 | Gorsek | |
| 6,447,809 B1 * | 9/2002 | Krumhar et al. | |
| 6,451,341 B1 * | 9/2002 | Slaga et al. | |
| 6,461,607 B1 * | 10/2002 | Farmer | |
| 6,534,063 B1 * | 3/2003 | Fallon | |
| 7,153,503 B1 * | 12/2006 | Henderson | |

FOREIGN PATENT DOCUMENTS

CN           1096457       * 12/1994

* cited by examiner

*Primary Examiner*—Michael Meller
(74) *Attorney, Agent, or Firm*—Thorpe North & Western, LLP

(57) ABSTRACT

The present invention provides a nutrient absorption enhancing composition that contains a mixture of various *Aspergillus* derived enzymes and mineral cofactors. In one aspect, the enzymes of the formulation may include protease, lipase, amylase, and cellulase. In another aspect, the mineral cofactors of the formulation may include calcium compounds, zinc compounds, manganese compounds, and magnesium compounds.

31 Claims, No Drawings

NUTRIENT ABSORPTION ENHANCING COMPOSITIONS AND METHODS

PRIORITY DATA

This application is a continuation of U.S. patent application Ser. No. 09/989,980 filed Nov. 20, 2001, now abandoned which is incorporated herein by reference.

THE FIELD OF THE INVENTION

The present invention relates generally to compositions and methods for enhancing nutrient absorption. More particularly, it concerns mineral and enzyme compositions, which increase digestion and nutrient absorption.

BACKGROUND OF THE INVENTION

Enzymes have become well known for their catalytic role in many biological functions. In general, catalysts lower the energy of activation required for a chemical reaction to proceed, thereby facilitating the start of a reaction, as well as enhancing the reaction's speed and efficiency. Often, these factors of speed and efficiency may dictate the biological value of a chemical reaction, and produce varying physiological results.

One of the most common reactions which enzymes catalyze is the hydrolysis, or digestion, of various nutrients such as proteins, lipids, and carbohydrates into smaller constituents. Such digestion is required in order for most organisms to utilize these substances in carrying on essential metabolic functions. Other chemical reactions involved in metabolic function, such as the production of ATP and gene reproduction, are also highly dependent on various enzymes.

Enzymes may be isolated or derived from a variety of sources, including animal tissue and products, fungi, bacteria, and plants. One example is the digestive enzyme pepsin, which was first isolated from the stomach and intestinal lining of pigs. Other examples of digestive enzymes include papian, which is derived from papaya plant, and bromelain, which is derived from pineapple.

Some enzymes are independently capable of asserting a catalytic effect. Other enzymes may not achieve catalytic activity without the presence of a second substance, or cofactor. Still other enzymes may be capable of asserting a catalytic effect without a cofactor, but have their potency and efficiency enhanced when the proper cofactor is present. Other variables, such as conditions of the physiologic environment, may also affect the catalytic activity of an enzyme. For example, many enzymes show little activity at a low pH, but become increasingly active as pH rises.

Environment not only affects the activity of many enzymes, but may also affect their stability. Harsh or extreme, physiologic conditions may destabilize many enzymes to the point that they lose their chemical and structural integrity and become incapable of exerting a catalytic effect. For example, both bromelain and papian display low tolerance for the pH extremes of the human digestive system. As such, when ingested orally, bromelain and papian lose much of their ability to aid in the digestion of food and attendant absorption of nutrients. In fact many enzymes experience such degradation when subjected to the environment of the stomach.

SUMMARY OF THE INVENTION

It has been recognized that enzymes that are able to survive the environment of the stomach, and actively catalyze hydrolysis of nutrients in the lower gastrointestinal tract, as well as in the blood stream would be desirable. Accordingly, the present invention provides a nutrient absorption increasing composition including: a) a protein hydrolysis catalyzing amount of an *Aspergillus* derived protease, and a catalysis enhancing calcium compound cofactor; b) a lipid hydrolysis catalyzing amount of an *Aspergillus* derived lipase, and a catalysis enhancing zinc compound cofactor; c) a cellulose hydrolysis catalyzing amount of an *Aspergillus* derived cellulase, and a catalysis enhancing manganese compound cofactor; and d) a starch hydrolysis catalyzing amount of an *Aspergillus* derived amylase, and a catalysis enhancing magnesium compound cofactor.

A variety of *Aspergillus* species may be used to derive the enzymes of the present composition. Examples include without limitation, *A. Niger, A. Oryzae, A. Acuileatus, A. Ochraceous, A. Terreus, A. Fumigatus, A. Flavus, A. Ustus, A. Versicolor*, and mixtures thereof.

A wide variety of calcium compounds may be used to present a sufficient amount of calcium to enhance the catalytic action of the protease. Examples of such calcium compounds include without limitation: calcium ascorbate, calcium citrate, calcium carbonate, calcium chloride, calcium oxide, calcium hydroxide, calcium gluconate, calcium lactate, calcium phosphate, calcium stearate, calcium sulfate, calcium amino acid chelates, and mixtures thereof.

Various zinc compounds may be employed in the composition of the present invention to present an amount of zinc that is sufficient to enhance the catalytic action of the lipase. Examples of such zinc compounds include without limitation: zinc gluconate, zinc oxide, zinc carbonate, zinc stearate, zinc sulfate, zinc amino acid chelates, and mixtures thereof.

Several manganese compounds may be employed in the composition of the present invention to present an amount of manganese that is sufficient to enhance the catalytic action of the cellulase. Examples of such manganese compounds include without limitation: manganese citrate, manganese gluconate, manganese chloride, manganese sulfate, manganese amino acid chelates, and mixtures thereof.

A wide variety of magnesium compounds may be employed in the composition of the present invention to present an amount of magnesium that is sufficient to enhance the catalytic action of the amylase. Examples of such magnesium compounds include without limitation: magnesium citrate, magnesium oxide, magnesium stearate, magnesium carbonate, magnesium chloride, magnesium gluconate, magnesium hydroxide, magnesium phosphate, magnesium sulfate, magnesium amino acid chelates, and mixtures thereof.

In one aspect of the invention, the nutrient absorption increasing composition may include: a) an amount of *Aspergillus* derived protease having a protein hydrolyzing activity of from about 1,000 HUT, to about 60,000 HUT, and a calcium compound cofactor which presents calcium in a ratio of at least about 1 mg of calcium for every 1200 HUT of protease activity; b) an amount of an *Aspergillus* derived lipase having a lipid hydrolyzing activity of from about 10 LU to about 800 LU, and a zinc compound cofactor which presents zinc in a ratio of at least about 1 mg of zinc for every 800 LU of lipase activity; c) an amount of an *Aspergillus* derived cellulase having a cellulose hydrolyzing activity of from about 3 CU to about 400 CU, and a manganese compound cofactor which presents manganese in a ratio of at least about 1 mg manganese for every 400 CU of cellulase activity; and d) an amount of an *Aspergillus* derived amylase having a starch hydrolyzing activity of from about 1,000 DU to about 20,000 DU, and a magnesium compound cofactor which presents magnesium in a ratio of at least about 1 mg magnesium for every 20,000 DU of amylase activity.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

DETAILED DESCRIPTION

Before the present nutrient absorption enhancing compositions, and accompanying methods are disclosed and described, it is to be understood that this invention is not limited to the particular design and materials disclosed herein, but is extended to equivalents thereof as would be recognized by those ordinarily skilled in the relevant arts. It should also be understood that terminology employed herein is used for the purpose of describing particular embodiments only, and is not intended to be limiting.

It must be noted that, as used in this specification and the appended claims, the singular forms "a," and, "the" include plural referents unless the context clearly dictates otherwise. Thus, for example, reference to a composition containing "an enzyme" includes one or more of such enzymes, and reference to "a mineral" includes reference to one or more of such minerals.

A. DEFINITIONS

In describing and claiming the present invention, the following terminology will be used in accordance with the definitions set forth below.

As used herein, "nutrient" refers to any substance that supplies the body with elements that are necessary for, or contribute to, metabolism and the performance of bodily functions and processes. Examples of nutrients include, without limitation, protein, carbohydrates, fats (lipids), vitamins, etc.

As used herein, "hydrolysis catalyzing amount" refers to the minimum amount of an enzyme, which is sufficient to catalyze the hydrolysis of its corresponding nutrient to a selected degree. Many methods for determining the minimum amount of an enzyme required to catalyze the hydrolysis of a selected amount of a corresponding nutrient are known in the art, and many may be found in the Institute of Medicine's publication *Food Chemicals Codex* (4$^{th}$ ed. 1996). Examples of such methods are recited below in the definitions of activity units for each of the enzymes contained in the present composition, such as HUT, DU, DP, SU, LU, etc.

As used herein, "cofactor" refers to an agent that activates an enzyme. Various substances act as specific cofactors for certain enzymes. Examples of cofactors that can be used with the enzymes employed in the present invention include without limitation minerals, such as calcium, zinc, manganese, and magnesium.

As used herein, "catalysis enhancing amount" of a cofactor refers to the minimum amount of cofactor, which is sufficient to enhance the catalytic action of an enzyme upon hydrolysis of a nutrient. Methods for determining the amount of a cofactor that is necessary to achieve a desired increase in catalysis are known to those skilled in the art. See, for example, Enzymes & Enzyme Therapy, Page 125, Keats publishing 1994; The Merck Manual 16th Edition, Page 907, 1992; and Enzymes The Fountain of Life, Dr. R. M. Williams, Page 165, Neville Press 1994, each of which is incorporated by reference herein.

As used herein, "*Aspergillus*" refers to any species of fungi in the genus *Aspergillus nidulans*. Examples of species include without limitation, *A. Niger, A. Oryzae, A. Ochraceous, A. Terreus, A. Fumigatus, A. Ustus, A. Flavus*, and *A. Versicolor*.

As used herein, "calcium," or "calcium compound" refer to a calcium-containing compound, which provides a sufficient source of calcium to enhance the catalytic action of an *Aspergillus* derived protease. Examples of calcium compounds include, without limitation, calcium ascorbate, calcium citrate, calcium carbonate, calcium amino acid chelates, and mixtures thereof.

As used herein, "zinc," or "zinc compound" refer to a zinc-containing compound, which provides a sufficient source of zinc to enhance the catalytic action of an *Aspergillus* derived lipase. Examples of zinc compounds include, without limitation, zinc gluconate, zinc oxides, zinc amino acid chelates, and mixtures thereof.

As used herein, "manganese," or "manganese compound" refer to a manganese-containing compound, which provides a sufficient source of manganese to enhance the catalytic action an *Aspergillus* derived cellulase. Examples of manganese compound include, without limitation, manganese citrate, manganese gluconate, manganese amino acid chelates, and mixtures thereof.

As used herein, "magnesium," or "magnesium compound" refer to a magnesium-containing compound, which provides a sufficient source of magnesium to enhance the catalytic action of an *Aspergillus* derived amylase. Examples of magnesium compounds include, without limitation, magnesium citrate, magnesium oxide, magnesium stearate, magnesium amino acid chelates, and mixtures thereof.

As used herein, "protein hydrolyzing activity," "hydrolyzing activity," "enzyme activity," and "activity" may be used interchangeably, and refer to the amount of hydrolyzing action that a given enzyme asserts on a corresponding nutrient. Various methods for quantifying enzyme activity are known to those skilled in the art, and are contained in the Food Chemicals Codex. Examples of various methods for measuring the activity of the specific enzymes used in the present composition are set forth below.

As used herein, "Dextrinizing Unit," or "DU" refers to the quantity of alpha-amylase required to dextrinize soluble starch in the presence of an excess of beta-amylase at the rate of 1 gram per hour at 30 degrees C.

As used herein, "Lipase Unit," or "LU" refers to the quantity of lipase enzyme required to liberate the equivalent of 1 mol of acid (H+) per minute of the substrate, under the conditions of the assay specified in the Food Chemicals Codex.

As used herein, "Cellulase Activity," or "CA" refers to the amount of cellulase enzyme required to reduce the viscosity of 200 g of a 5% solution of the specified sodium carboxymethylcellulose substrate from 400 to 300 cps at 35 degrees plus or minus 1 degree, in 1 hour.

As used herein, "Hemoglobin Units on the Tyrosine Basis," or "HUT" refers to the amount of an enzyme that produces in 1 minute under specified conditions, a hydrolysate having an absorbance at 275 nm, which is the same as a solution containing 1.10 g per ml of tyrosine in 0.006 of hydrochloric acid.

As used herein, "DP" refers to the amount of a maltase enzyme that hydrolyzes a specified* amount of starch substrate at a pH of 4.6 at 20 degrees C. in 30 minutes (*Amounts are set forth under the FCC guidelines) The resultant sugar groups are measured in a titrimetric procedure using alkaline ferricyanide.

As used herein, "Sucrase Units," "SU," "Invertase Activity," or "IA" may be used interchangeably, and refer to the amount of sucrase enzyme required to hydrolyze 77% of a specified* sucrose amount (*amounts are set forth under the FCC guidelines), applied under the conditions of the assay.

As used herein, "LacU," refers to the quantity of lactase that will liberate 1 mol of o-nitrophenol per minute under the conditions of the assay specified in the Food Chemicals Codex.

Du, Lu, CA, DP, SU, LacU, and HUT are all standardized units of measurement for enzyme activity and set forth in the *Food Chemicals Codex*, (4th ed. 1996), which is published by the Institute of Medicine, and is incorporated herein by reference. As such, the meaning and use of each is readily apparent to one skilled in the art.

As used herein, "protease" refers to an enzyme, which catalyzes the hydrolysis of proteins.

As used herein, "lipase" refers to an enzyme, which catalyzes the hydrolysis of lipids and fats.

As used herein, "amylase" refers to an enzyme, which catalyzes the hydrolysis of starch.

As used herein, "cellulose" refers to an enzyme, which catalyzes the hydrolysis of cellulose.

As used herein, "maltase" refers to an enzyme, which catalyzes the hydrolysis of maltose into glucose.

As used herein, "sucrase" and "invertase" may be used interchangeably, and refer to an enzyme, which catalyzes the hydrolysis of sucrose into glucose and fructose.

Numerous examples of enzyme sources and methods of producing the above-recited enzymes, such as fermentation, and extraction from plant and animal sources are well known to those of ordinary skill in the art. Further, examples of various enzymes, their sources and methods for their production are found in the Food Chemicals Codex, (4th ed. 1996), which is incorporated herein by reference.

Concentrations, amounts, solubilities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, an enzyme activity range of about 1,000 HUT to about 60,000 HUT should be interpreted to include not only the explicitly recited concentration limits of 1,000 HUT to about 60,000 HUT, but also to include individual concentrations such as 4,000 HUT, 10,000 HUT, 20,000 HUT and sub-ranges such as 5,000 HUT to 30,000 HUT, 10,000 HUT to 20,000 HUT, etc. The same principle applies to ranges reciting only one numerical value, such as "at least about 2,500 HUT," which should be interpreted to include all of the above-recited values and ranges. Further, such an interpretation should apply regardless of the breadth of the range or the characteristic being described, such as enzyme activity, mineral amount, and amounts and concentrations of other ingredients, or agents.

B. THE INVENTION

The nutrient absorption enhancing composition of the present invention generally includes a hydrolysis-catalyzing amount of at least one *Aspergillus* derived enzyme. When administered to the body, such enzymes increase the digestion, or break down of nutrients, and thus enhance the body's ability to absorb and use the constituent parts. As such, the body becomes capable of using more of the nutrients ingested, as well as absorbing them at an increased rate.

While many digestive enzymes become inactivated or destroyed by the low pH of the stomach, *Aspergillus* derived enzymes are active at a pH as low as 1 or 2, and survive beyond the stomach to be active in the intestine and blood stream. Thus, *Aspergillus* derived enzymes are significantly more efficacious than many other digestive enzymes, such as bromelain and papian. Such effectiveness allows the *Aspergillus* derived enzymes to be used in a variety of specific treatment applications. By way of example, without limitation, *Aspergillus* derived lipase may be used to reduce blood serum fats like triglycerides, and low-density lipids. Further, *Aspergillus* derived amylase and cellulase may be used to reduce blood sugar levels.

In addition to the *Aspergillus* derived enzyme, the present composition generally includes one or more catalysis enhancing cofactors. While many *Aspergillus* derived enzymes display significant hydrolyzing activity without a cofactor, it has been recognized that the catalytic action responsible for the hydrolyzing activity may be enhanced by the presence of an appropriate cofactor. As such, digestion times may be decreased, and the efficiency of nutrient absorption increased.

Various combinations of *Aspergillus* derived enzymes, and catalysis enhancing cofactors, may be included in the present composition order to achieve desired metabolic results. In one aspect of the invention, the *Aspergillus* derived enzyme may be a protease, and the cofactor may be a calcium compound. In another aspect, the *Aspergillus* derived enzyme may be a lipase, and the cofactor may be a zinc compound. In yet another aspect, the *Aspergillus* derived enzyme may be a cellulase, and the cofactor may be a manganese compound. In a further aspect, the *Aspergillus* derived enzyme may be an amylase, and the cofactor may be a magnesium compound.

In addition to single enzymes, the composition of the present invention may include a combination of enzymes and cofactors. Combinations of enzymes have been found to be advantageous in achieving several desired results simultaneously, the conglomeration of which, significantly contribute to an individuals overall health and well being. In one aspect, the composition of the present invention may include: a) a protein hydrolysis catalyzing amount of an *Aspergillus* derived protease, and a catalysis enhancing calcium compound cofactor; b) a lipid hydrolysis catalyzing amount of an *Aspergillus* derived lipase, and a catalysis enhancing zinc compound cofactor; c) a cellulose hydrolysis catalyzing amount of an *Aspergillus* derived cellulase, and a catalysis enhancing manganese compound cofactor; and d) a starch hydrolysis catalyzing amount of an *Aspergillus* derived amylase, and a catalysis enhancing magnesium compound cofactor.

A wide variety of *Aspergillus* species may be used for the production of the various *Aspergillus* enzymes included in the composition of the present invention. General techniques for the production of enzymes from various sources, including *Aspergillus* fungi, by culturing, extracting, and purifying, are well known to those ordinarily skilled in the art.

Further, many enzymes, such as *Aspergillus* derived enzymes may be obtained in quantity from various commercial sources, such as Bio-Cat, Inc., Louisa, Va., Amano International Enzyme Company (AIE), Troy, Va., and National Enzyme Company, Forsythe, Mo.

Examples of *Aspergillus* fungi species that may be used to derive the enzymes of the present composition include without limitation, *A. Niger, A. Oryzae, A. Acuileatus, A. Ochraceous, A. Terreus, A. Fumigatus, A. Flavus, A. Ustus, A. Versicolor*, and mixtures thereof. In one aspect, the *Aspergillus* may be a combination of *A. Niger* and *A. Oryzae* species. In another aspect, the *Aspergillus* species may be *A. Niger*. In a further aspect, the *Aspergillus* species may be *A. Oryzae*.

As is known to those skilled in the art, each particular enzyme may have one or more specific cofactors that enhance the efficacy of the enzyme. In general, the predictability of cofactors for enzymes is low. Therefore, determination of suitable cofactors for specific enzymes has been the subject of much research.

The cofactors that have been found to enhance the enzymes of the present composition are generally metals. Particularly, calcium has been found to be a suitable cofactor for the *Aspergillus* derived protease. Zinc has been found to be a suitable cofactor for the *Aspergillus* derived lipase. Manganese has been found to be a suitable cofactor for the *Aspergillus* derived cellulase. Magnesium has found to be a suitable cofactor for the *Aspergillus* derived amylase. A wide variety of compounds contain these metals in a manner that makes them sufficiently bioavailable to enhance the catalyzing action of each enzyme.

As such, a variety of calcium compounds may be utilized by the present composition to enhance the catalytic action of the protease. Examples of calcium compounds that may be used include without limitation, calcium ascorbate, calcium citrate, calcium carbonate, calcium amino acid chelates, and mixtures thereof. In one aspect, the calcium compound may be calcium ascorbate.

Numerous zinc compounds may be used to enhance the catalytic action of the lipase in the present composition. Specific examples of acceptable zinc compounds include, but are not limited to, zinc gluconate, zinc oxide, zinc amino acid chelates, and mixtures thereof. In one aspect, the zinc compound may be zinc gluconate.

Various manganese compounds can be used to enhance the catalytic action of the cellulase in the present composition. Specific examples of suitable manganese compounds include without limitation, manganese citrate, manganese gluconate, manganese amino acid chelates, and mixtures thereof. In one aspect, the manganese compound may be manganese gluconate.

Several magnesium compounds may be used in the present composition to enhance the catalytic action of the alpha amylase. Specific examples of suitable magnesium compounds include, but are not limited to, magnesium citrate, magnesium oxide, magnesium stearate, magnesium amino acid chelates, and mixtures thereof. In one aspect, the magnesium compound may be magnesium compound is magnesium citrate.

The amount of each *Aspergillus* derived enzyme contained in the composition of the present invention may be dependent upon the desired results to be achieved. Enzymes are generally measured in units of activity or "activity units." Various procedures for quantifying the activity of a specific enzyme have been established by the Institute of Medicine, and are contained in the Food Chemicals Codex, as explained in the definitions section above. By following the procedures for determining the activity of a particular enzyme, one of ordinary skill in the art can readily determine the quantity of enzyme necessary in order to achieve a desired amount of activity. Alternatively, the enzymes obtained in quantity from the above-recited sources, may indicate the potency, or activity of a particular enzyme in terms of product quantity. As such one skilled in the art can determine how much of the purchased product will be required to obtain the desired enzyme activity.

In one aspect, the amount of *Aspergillus* derived protease included in the present composition may have a protein hydrolyzing activity of from at least about 1,000 HUT to about 60,000 HUT. In another aspect, the amount of protease may have a protein hydrolyzing activity of from about 2,500 HUT to about 30,000 HUT.

In one aspect, the amount of *Aspergillus* derived lipase included in the present composition may have a lipid hydrolyzing activity of from at least about 10 LU to about 800 LU. In another aspect, the amount of lipase may have a lipid hydrolyzing activity of from about 25 LU to about 400 LU.

In one aspect, the amount of *Aspergillus* derived cellulase included in the present composition may have a cellulose hydrolyzing activity of from at least about 3 CU to about 400 CU. In another aspect, the amount of cellulase may have a cellulose hydrolyzing activity of from about 6 CU to about 200 CU.

In one aspect, the amount of *Aspergillus* derived amylase included in the present composition may have a starch hydrolyzing activity of from at least about 1,000 DU to about 20,000 DU. In another aspect, the amount of amylase may have a starch hydrolyzing activity of from about 2,500 DU to about 10,000 DU.

The amount of cofactor required to enhance the catalytic action of each enzyme will generally correspond to the amount of enzyme present. Further, the amount of cofactor required may depend on the bioavailability of the metal presented by the particular metal containing compound. Those ordinarily skilled in the art will be able to readily determine the bioavailability of metals contained in various compounds, either from literary sources, or simple experimentation.

In one aspect the calcium compound cofactor included in the present composition may be present in a ratio of at least about 1 mg for every 1200 HUT of protease activity. In another aspect, the ratio may be from about 1 mg for every 200 HUT of protease to about 1 mg for every 600 HUT of protease activity.

In one aspect, the zinc compound cofactor included in the present composition may be present in a ratio of at least about 1 mg for every 800 LU of lipase activity. In another aspect, the ratio may be from about 1 mg for every 25 LU of lipase to about 1 mg for every 400 LU of lipase activity.

In one aspect, the manganese compound cofactor included in the present composition may be present in a ratio of at least about 1 mg for every 400 CU of cellulase activity. In another aspect, the ratio may be from about 1 mg for every 4 CU of cellulase to about 1 mg for every 200 CU of cellulase activity.

In one aspect, the magnesium compound cofactor included in the present composition may be present in a ratio of at least about 1 mg for every 20,000 DU of amylase activity. In another aspect, the ratio may be from about 1 mg for every 1,000 DU of amylase to about 1 mg for every 10,000 DU of amylase activity.

In addition to the enzymes recited above, the composition of the present invention may include other *Aspergillus* derived enzymes in various hydrolysis-catalyzing amounts, such as maltase, lactase, and sucrase. Such enzymes may be added in order to achieve a particularly desired result. Procedures for quantifying the activity for such enzymes may be found in the Food Chemicals Codex, and is also explained in the above-recited definitions.

In one aspect, the present composition may include a maltose hydrolysis-catalyzing amount of an *Aspergillus* derived maltase. In another aspect, the amount of *Aspergillus* derived maltase may have a maltose hydrolyzing activity from at least about 50 DP to about 300 DP.

In one aspect, the present composition may include a lactose hydrolysis-catalyzing amount of an *Aspergillus* derived lactase. In another aspect, the amount of *Aspergillus* derived lactase has a lactose hydrolyzing activity of from at least about 200 LacU to about 600 LacU.

In one aspect, the present composition may include a sucrose hydrolysis-catalyzing amount of an *Aspergillus* derived sucrase. In another aspect, the amount of sucrase has a sucrose hydrolyzing activity of from at least about 50 SU to about 200 SU.

As explained above, a single *Aspergillus* derived enzyme and a corresponding cofactor may be used as the composition of the present invention, or the composition may contain a combination of *Aspergillus* derived enzymes and corresponding cofactors. In one aspect, the nutrient absorption increasing composition of the present invention may include: a) an amount of *Aspergillus* derived protease having a protein hydrolyzing activity of from about 1,000 HUT, to about 60,000 HUT, and a calcium compound cofactor in a ratio of at least about 1 mg for every 1200 HUT of protease activity; b) an amount of an *Aspergillus* derived lipase having a lipid hydrolyzing activity of from about 10 LU to about 800 LU, and a zinc compound cofactor in a ratio of at least about 1 mg for every 800 LU of lipase activity; c) an amount of an *Aspergillus* derived cellulase having a cellulose hydrolyzing activity of from about 3 CU to about 400 CU, and a manganese compound cofactor in a ratio of at least about 1 mg for every 400 CU of cellulase activity; and d) an amount of an *Aspergillus* derived amylase having a starch hydrolyzing activity of from about 1,000 DU to about 20,000 DU, and a magnesium compound cofactor in a ratio of at least about 1 mg for every 20,000 DU of amylase activity. Other enzymes such as the maltase, lactase, etc. may be added in desired quantity to achieve specific results.

In addition to the enzyme and cofactor combinations enumerated above, the composition of the present invention may include various nutrients and other positive health-imparting agents for co-delivery with the enzymes and cofactors. Such substances may be derived from a variety of sources, both natural and synthetic. Examples of natural sources of nutrients and positive health-imparting agents include without limitation, botanical extracts, fungi extracts, and animal or insect products. Examples of botanical extracts may include any part of a plant, herb, tree, or vegetable that contains a useful bioactive substance, including but not limited to seeds, leaves, stem, bark, roots, sap, and fruit. Examples of animal or inset products include products produced by animals, such as milk, eggs, etc., as well as products obtained by sacrificing and harvesting the animal itself, such as meat, blood, intestines, carcass, etc. Various sources of fungi are known to have positive health benefit imparting, or nutritious properties, such a mushrooms of various types.

In addition to a nutrient absorption enhancing composition, the present invention encompasses a method for enhancing nutrient absorption in an animal. In one aspect, such a method includes the step of administering a nutrient absorption enhancing composition as set forth herein. Such an administration may be performed by various routes, including oral, transdermal, transmucosal, and parenteral routes of administration.

C. EXAMPLES

The following examples are intended to be merely illustrative of the various aspects of the invention disclosed herein and are not intended in any way to limit the scope of the claimed invention. Other aspects of the invention that are considered equivalent by those skilled in the art are also within the scope of this invention.

Example 1

| Ingredient | Activity/bioavail. | Amount |
|---|---|---|
| *Aspergillus* protease | 2500 HUT | 38 mg |
| Calcium Ascorbate | 12.5 mg (100%) | 12.5 mg |
| *Aspergillus* lipase | 50 LU | 250 ug |
| Zinc Gluconate | 3.75 mg (13%) | 29 mg |
| *Aspergillus* cellulase | 6 CU | 120 ug |
| Manganese Gluconate | 1.25 mg (11.4%) | 11 mg |
| *Aspergillus* Amylase | 2500 DU | 25 mg |
| Magnesium Citrate | 2.5 mg (20%) | 13 mg |
| Total Formulation: | | 128.87 mg |

Example 2

| Ingredient | Activity/bioavail. | Amount |
|---|---|---|
| *Aspergillus* protease | 2500 HUT | 38 mg |
| Calcium Ascorbate | 15 mg (100%) | 15 mg |
| *Aspergillus* lipase | 50 LU | 250 ug |
| Zinc Gluconate | 5 mg (13%) | 38 mg |
| *Aspergillus* cellulase | 6 CU | 120 ug |
| Manganese Gluconate | 5 mg (11.4%) | 44 mg |
| *Aspergillus* Amylase | 2500 DU | 25 mg |
| Magnesium Citrate | 5 mg (20%) | 25 mg |
| Betaine HCl | 5 mg | 5 mg |
| Total Formulation: | | 190.67 mg |

Example 3

| Ingredient | Activity/bioavail. | Amount |
|---|---|---|
| *Aspergillus* protease | 10,000 HUT | 16 mg |
| Calcium Ascorbate | 15 mg (100%) | 15 mg |
| *Aspergillus* lipase | 200 LU | 1 mg |
| Zinc Gluconate | 5 mg (13%) | 38 mg |
| *Aspergillus* cellulase | 50 CU | 1 mg |
| Manganese Gluconate | 5 mg (11.4%) | 44 mg |
| *Aspergillus* Amylase | 10,000 DU | 20 mg |
| Magnesium Citrate | 5 mg (20%) | 25 mg |
| Betaine HCl | 5 mg | 5 mg |
| Total Formulation: | | 165 mg |

Example 4

| Ingredient | Activity/bioavail. | Amount |
|---|---|---|
| *Aspergillus* protease | 30,000 HUT | 60 mg |
| Calcium Ascorbate | 15 mg (100%) | 15 mg |
| *Aspergillus* lipase | 400 LU | 2 mg |
| Zinc Gluconate | 5 mg (13%) | 38 mg |
| *Aspergillus* cellulase | 200 CU | 4 mg |
| Manganese Gluconate | 5 mg (11.4%) | 44 mg |
| *Aspergillus* Amylase | 8,000 DU | 80 mg |
| Magnesium Citrate | 5 mg (20%) | 25 mg |
| Malt Diastase | 150 DP | 66 mg |
| *Aspergillus* Lactase | 400 LacU | 4 mg |
| *Aspergillus* Sucrase | 700 SU | 4 mg |
| Betaine HCl | 5 mg | 5 mg |
| Kelp | Filler | 15 mg |
| Black Humic Mineral | 25 mg | 25 mg |
| Apple Pectin | 15 mg | 15 mg |
| Total Formulation: | | 402 mg |

Example 5

| Ingredient | Amount |
|---|---|
| Cat's Claw | 100 mg |
| Astragalus | 100 mg |
| Reishi Mushroom | 20 mg |
| Shitake Mushroom | 15 mg |
| Maitake Mushroom | 30 mg |
| Aloe Vera Leaf | 50 mg |
| Royal Jelly 3X | 50 mg |
| Enzyme/Mineral Formulation of Example 2 | 165 mg |
| Cranberry Extract | 20 mg |
| Total Formulation: | 550 mg |

Example 6

| Ingredient | Amount |
|---|---|
| Grape Seed extract 95% | 30 mg |
| Co-Q10 | 10 mg |
| Beta Carotene | 2500 IU |
| Enzyme/Mineral Formulation of Example 2 | 165 mg |
| Bilberry | 10 mg |
| Kelp | 50 mg |
| Total Formulation: | 275 mg |

Example 7

| Ingredient | Amount |
|---|---|
| Black Walnut Hulls | 25 mg |
| Pau D'Arco | 25 mg |
| Goldenseal Root | 5 mg |
| Artesemia Annua | 10 mg |
| Maitake Mushroom | 30 mg |
| Sarsaparilla | 15 mg |
| Garlic | 116 mg |
| Aloe Vera 200:1 | 5 mg |
| Cloves | 25 mg |
| Enzyme/Mineral Formulation of Example 2 | 165 mg |
| Total Formulation: | 421 mg |

Example 8

| Ingredient | Amount |
|---|---|
| Milk Thistle | 50 mg |
| Safflower Petals | 15 mg |
| *Psyllium* Seed Husks | 100 mg |
| Senna Leaf | 15 mg |
| Apple Pectin | 10 mg |
| Acacia Gum | 10 mg |
| Marshmallow | 10 mg |
| Goldenseal Root | 15 mg |
| Dandelion Root | 30 mg |
| Garlic | 20 mg |
| Red Clover Tops | 50 mg |
| Cascara Segrada | 10 mg |
| Enzyme/Mineral Formulation of Example 2 | 165 mg |
| Kelp | 25 mg |
| Total Formulation: | 525 mg |

Example 9

Using the cholestech CDX CLIA approved testing monitor, twelve individuals with type II diabetes were selected and placed into 3 groups of equal numbers. Each group ranged in age from mid 30's to mid 60's and consisted of two female and two male subjects, and designated Groups A, B, and C. The blood sugar levels of each individual were tested approximately one hour after eating a carbohydrate meal of 150 grams. Table 1 shows the blood sugar levels of each individual and group.

TABLE 1

| Group A | Group B | Group C |
|---|---|---|
| 234 | 225 | 240 |
| 180 | 232 | 210 |
| 255 | 198 | 252 |
| 230 | 210 | 248 |
| 224.75 | 216.25 | 237.5 |

Following initial testing, each group was asked to follow their normal insulin regimen as prescribed by their physicians. The individuals of Group A, designated as the baseline group and given nothing. The individuals of Group B, were given a placebo, and the individuals of Group C were given the formulation of Example 4 above. The individuals taking the placebo, and those taking the mineral and enzyme formulation were placed on a regimen of four (4) 250 mg capsules per day. One capsule was taken with each meal and one before going to bed. After two weeks, blood samples were again collected. The results of this sampling are shown in Table 2.

TABLE 2

| Group A | Group B | Group C |
|---------|---------|---------|
| 225 | 228 | 225 |
| 200 | 230 | 189 |
| 240 | 185 | 210 |
| 235 | 215 | 195 |
| 225 | 214.5 | 204.75 |

These results show that administration of the mineral enzyme formulation to the individuals in Group C resulted in a 13% reduction in blood sugar levels.

The above-recited dosage regimens were then continued for an additional two weeks, and blood sugar levels were once again measured. The results of the measurement are shown in Table 3.

TABLE 3

| Group A | Group B | Group C |
|---------|---------|---------|
| 230 | 233 | 215 |
| 195 | 242 | 190 |
| 245 | 196 | 189 |
| 232 | 210 | 185 |
| 225.5 | 220.25 | 192.75 |

These results show that over the 30 day testing period, the individuals in Group C averaged an 18% drop in blood sugar levels by taking the mineral and enzyme formulation of Example 4.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A nutrient absorption increasing composition comprising:
    a) an amount of *Aspergillus* derived protease having a protein hydrolyzing activity of from about 1,000 HUT, to about 60,000 HUT, and a calcium compound cofactor which provides calcium in a ratio of at least about 1 mg of calcium for every 1200 HUT of protease activity;
    b) an amount of an *Aspergillus* derived lipase having a lipid hydrolyzing activity of from about 10 LU to about 800 LU, and a zinc compound cofactor which provides zinc in a ratio of at least about 1 mg of zinc for every 800 LU of lipase activity;
    c) an amount of an *Aspergillus* derived cellulase having a cellulose hydrolyzing activity of from about 3 CU to about 400 CU, and a manganese compound cofactor which provides manganese in a ratio of at least about 1 mg of manganese for every 400 CU of cellulase activity; and
    d) an amount of an *Aspergillus* derived amylase having a starch hydrolyzing activity of from about 1,000 DU to about 20,000 DU, and a magnesium compound cofactor which provides magnesium in a ratio of at least about 1 mg of magnesium for every 20,000 DU of amylase activity.

2. The composition of claim 1, wherein the *Aspergillus* is a species selected from the group consisting of: *A. Niger, A. Oryzae, A. Acuileatus, A. Ochraceous, A. Terreus, A. Fumigatus, A. Flavus, A. Ustus, A. Versicolor*, and mixtures thereof.

3. The composition of claim 2, wherein the *Aspergillus* is a combination of *A. Niger* and *A. Oryzae* species.

4. The composition of claim 2, wherein the *Aspergillus* is *A. Niger* species.

5. The composition of claim 2, wherein the *Aspergillus* is *A. Oryzae* species.

6. The composition of claim 1, wherein the calcium compound is a member selected from the group consisting of: calcium ascorbate, calcium citrate, calcium carbonate, calcium amino acid chelates, and mixtures thereof.

7. The composition of claim 6, wherein the calcium compound is calcium ascorbate.

8. The composition of claim 1, wherein the zinc compound is a member selected from the group consisting of: zinc gluconate, zinc oxide, zinc amino acid chelates, and mixtures thereof.

9. The composition of claim 8, wherein the zinc compound is zinc gluconate.

10. The composition of claim 1, wherein the manganese compound is a member selected from the group consisting of manganese citrate, manganese gluconate, manganese amino acid chelates, and mixtures thereof.

11. The composition of claim 10, wherein the manganese compound is manganese gluconate.

12. The composition of claim 1, wherein the magnesium compound is a member selected from the group consisting of: magnesium citrate, magnesium oxide, magnesium stearate, magnesium amino acid chelates, and mixtures thereof.

13. The composition of claim 12, wherein the magnesium compound is magnesium citrate.

14. The composition of claim 1, wherein the protein hydrolyzing activity is from about 2,500 HUT to about 30,000 HUT.

15. The composition of claim 1, wherein the lipid hydrolyzing activity is from about 25 LU to about 400 LU.

16. The composition of claim 1, wherein the cellulose hydrolyzing activity is from about 6 CU to about 200 CU.

17. The composition of claim 1, wherein the starch hydrolyzing activity is from about 2500 DU to about 10,000 DU.

18. The composition of claim 1, wherein the ratio is from about 1 mg of calcium for every 200 HUT of protease to about 1 mg of calcium for every 600 HUT of protease activity.

19. The composition of claim 1, wherein the ratio is from about 1 mg of zinc for every 25 LU of lipase to about 1 mg of zinc for every 400 LU of lipase activity.

20. The composition of claim 1, wherein the ratio is from about 1 mg of manganese for every 4 CU of cellulase to about 1 mg of manganese for every 200 CU of cellulase activity.

21. The composition of claim 1, wherein the ratio is from about 1 mg of magnesium for every 1,000 DU of amylase to about 1 mg of magnesium for every 10,000 DU of amylase activity.

22. The composition of claim 1, further comprising a maltose hydrolysis catalyzing amount of an *Aspergillus* derived maltase.

23. The composition of claim 22, wherein the amount of *Aspergillus* derived maltase has a maltose hydrolyzing activity from at least about 50 DP to about 300 DP.

24. The composition of claim 1, further comprising a lactose hydrolysis catalyzing amount of an *Aspergillus* derived lactase.

25. The composition of claim 24, wherein the amount of *Aspergillus* derived lactase has a lactose hydrolyzing activity of from at least about 200 LacU to about 600 LacU.

26. The composition of claim 1, further comprising a sucrose hydrolysis catalyzing amount of an *Aspergillus* derived sucrase.

27. The composition of claim 26, wherein the amount of sucrase has a sucrose hydrolyzing activity of from at least about 50 SU to about 200 SU.

28. The composition of claim 1, wherein the amount of *Aspergillus* derived protease has a protein hydrolyzing activity of from at least about 1,000 HUT to about 60,000 HUT.

29. The composition of claim 1, wherein the amount of *Aspergillus* derived lipase has a lipid hydrolyzing activity of from at least about 10 LU to about 800 LU.

30. The composition of claim 1, wherein the amount of *Aspergillus* derived celluloase has a cellulose hydrolyzing activity of from at least about 3 CU to about 400 CU.

31. The composition of clam 1, wherein the amount of *Aspergillus* derived amylase has a starch hydrolyzing activity of from at least about 1,000 DU to about 20,000 HU.

* * * * *